United States Patent [19]

King

[11] Patent Number: 4,822,795

[45] Date of Patent: Apr. 18, 1989

[54] PHARMACEUTICALLY USEFUL ESTERS AND AMIDES

[75] Inventor: Francis D. King, Harlow, England

[73] Assignee: Beecham Group p.l.c., Brentford, England

[21] Appl. No.: 78,105

[22] Filed: Jul. 27, 1987

[30] Foreign Application Priority Data

Jul. 25, 1986 [CH] Switzerland ............... 8618149
Apr. 14, 1987 [CH] Switzerland ............... 8708940

[51] Int. Cl.$^4$ ............... A61K 31/46; C07D 451/04
[52] U.S. Cl. ............... 514/214; 514/215; 514/299; 514/300; 514/303; 514/304; 514/305; 540/582; 546/112; 546/120; 546/121; 546/126; 546/133; 546/183
[58] Field of Search ............... 546/120, 121, 112, 133, 546/126, 183; 540/582; 514/214, 215, 299, 300, 303, 304, 305

[56] References Cited

FOREIGN PATENT DOCUMENTS 564422 10/1958 Canada ............... 546/126
158265 10/1985 European Pat. Off.
2100259 12/1982 United Kingdom.
2125398 3/1984 United Kingdom.

Primary Examiner—Mary C. Lee
Assistant Examiner—Bernard I. Dentz
Attorney, Agent, or Firm—James F. Haley, Jr.; David K. Barr

[57] ABSTRACT

Compounds of formula (I), or a pharmaceutically acceptable salt thereof:

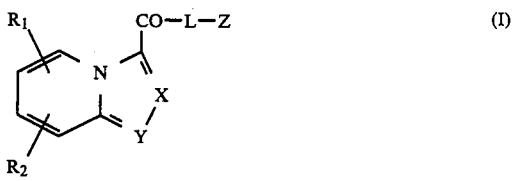

wherein
L is NH or O;
X is N or $CR_3$ wherein $R_3$ is hydrogen or $C_{1-6}$ alkoxy;
Y is N or $CR_4$ wherein $R_4$ is hydrogen, halogen, $CF_3$, $C_{1-6}$ alkyl, $C_{1-6}$ alkoxy, $C_{1-6}$ alkylthio, $C_{1-6}$ alkylsulphonyl, $C_{1-6}$ alkylsulphinyl, $C_{1-7}$ acyl, cyano, $C_{1-6}$ alkoxycarbonyl, $C_{1-7}$ acylamino, hydroxy, nitro or amino, aminocarbonyl, or aminosulphonyl, optionally N-substituted by one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;
$R_1$ and $R_2$ are independently selected from hydrogen, or halogen;
Z is a group of formula (a), (b) or (c):

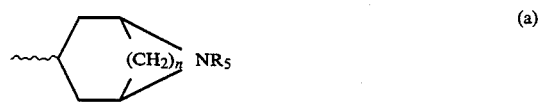

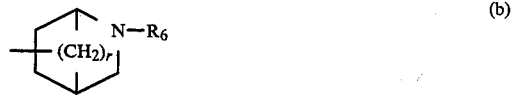

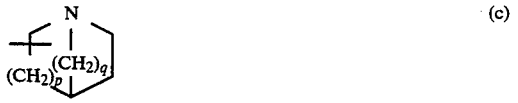

wherein
n is 2 or 3; p is 1 or 2; q is 1 to 3; r is 1 to 3; and $R_5$ or $R_6$ is $C_{1-4}$ alkyl; having 5-$HT_3$ antagonist activity, a process for their preparation and their use as pharmaceuticals.

9 Claims, No Drawings

PHARMACEUTICALLY USEFUL ESTERS AND AMIDES

This invention relates to novel compounds having useful pharmacological properties, to pharmaceutical compositions containing them, to a process and intermediates for their preparation, and to their use as pharmaceuticals.

GB Nos. 2100259A and 2125398A, and EP-A No. 158265 describe esters and amides having an azabicyclic side chain and possessing 5-HT$_3$ antagonist activity.

A class of novel, structurally distinct compounds has now been discovered. These compounds have 5-HT$_3$ antagonist activity.

Accordingly, the present invention provides a compound of formula (I), or a pharmaceutically acceptable salt thereof:

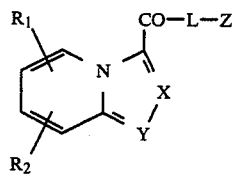

wherein
L is NH or O;
X is N or CR$_3$ wherein R$_3$ is hydrogen or C$_{1-6}$ alkoxy;
Y is N or CR$_4$ wherein R$_4$ is hydrogen, halogen, CF$_3$, C$_{1-6}$ alkyl, C$_{1-6}$ alkoxy, C$_{1-6}$ alkylthio, C$_{1-6}$ alkylsulphonyl, C$_{1-6}$ alkylsulphinyl, C$_{1-7}$ acyl, cyano, C$_{1-6}$ alkoxycarbonyl, C$_{1-7}$ acylamino, hydroxy, nitro or amino, aminocarbonyl, or aminosulphonyl, optionally N-substituted by one or two groups selected from C$_{1-6}$ alkyl, C$_{3-8}$ cycloalkyl, and C$_{3-8}$ cycloalkyl C$_{1-4}$ alkyl or disubstituted by C$_4$ or C$_5$ polymethylene; phenyl or phenyl C$_{1-4}$ alkyl group optionally substituted in the phenyl ring by one or two of halogen, C$_{1-6}$ alkoxy or C$_{1-6}$ alkyl groups;
R$_1$ and R$_2$ are independently selected from hydrogen, or halogen;
Z is a group of formula (a), (b) or (c):

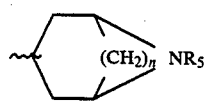

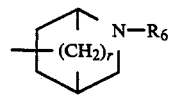

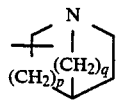

wherein n is 2 or 3; p is 1 or 2; q is 1 to 3; r is 1 to 3; and
R$_5$ or R$_6$ is C$_{1-4}$ alkyl.
Often L is NH.

Suitable values for X include N, or CR$_3^1$ wherein R$_3^1$ is hydrogen, methoxy, ethoxy, n- or iso-propoxy. Often X is N, CH or COMe.

Suitable values for Y include N, or CR$_4^1$ wherein R$_4^1$ is hydrogen, fluoro, chloro, bromo, CF$_3$, methyl, ethyl, methoxy, ethoxy, methylthio, ethylthio, methylsulphonyl, ethylsulphonyl, methylsulphinyl, ethylsulphinyl, acetyl, propionyl, cyano, methoxycarbonyl, ethoxycarbonyl, acetylamino, hydroxy, nitro; and amino, aminocarbonyl, or aminosulphonyl, any of which may be optionally substituted by one or two methyl groups or by a cyclopentyl or cyclohexyl group or R$_4^1$ is phenyl or benzyl optionally substituted by one or two methyl, methoxy, bromo, chloro or fluoro groups. Often Y is N, CH or CCH$_3$, preferably CCH$_3$.

Values for R$_1$ and/or R$_2$ include hydrogen, fluoro, chloro or bromo. Preferably R$_1$ and R$_2$ are both hydrogen.

Preferably n is 2 or 3 and p, q and r are 1 or 2.

Examples of R$_5$/R$_6$ include as groups of interest C$_{1-3}$ alkyl such as methyl, ethyl and n- and iso-propyl. R$_5$/R$_6$ is preferably methyl or ethyl, most preferably methyl.

There is a group of compounds within formula (I) wherein R$_4$ is hydrogen or C$_{1-6}$ alkyl and the remaining variables are as defined in formula (I).

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochlorid salt.

Examples of pharmaceutically acceptable salts include quaternary derivatives of the compounds of formula (I) such as the compounds quaternised by compounds R$_a$-T wherein R$_a$ is C$_{1-6}$ alkyl, phenyl-C$_{1-6}$ alkyl or C$_{5-7}$ cycloalkyl, and T is a radical corresponding to an anion of an acid. Suitable examples of R$_a$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of formula (I) may adopt an endo or exo configuration with respect to L. The endo configuration is preferred.

A group of compounds within formula (I) is of formula (II):

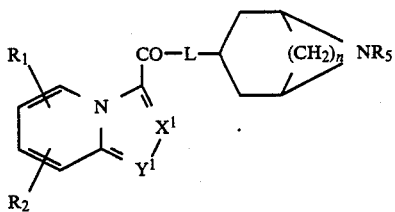

(II)

wherein $X^1$ is N, CH or $COCH_3$, $Y^1$ is N, or $C-R_4^1$ as defined and the remaining variables are as defined in formula (I).

Examples of the variables and preferred variables are as so described for corresponding variables in relation to formula (I).

A further group of compounds within formula (I) is of formula (III):

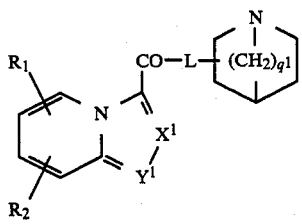

(III)

wherein $q^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

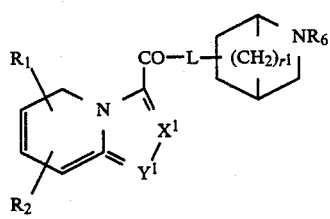

(IV)

wherein $r^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

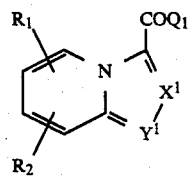

(V)

with a compound of formula (VI):

$$H-L-Z^1 \quad (VI)$$

or a reactive derivative thereof, when L is O; wherein $Q_1$ is a leaving group; $Z^1$ is Z as defined or wherein $R_5/R_6$ is replaced by a hydrogenolysable protecting group; and the remaining variables are as hereinbefore defined; and thereafter optionally converting any $R_1$ and/or $R_2$ group to another $R_1/R_2$ group respectively, converting $Z^1$, when other than Z, to Z; and optionally forming a pharmaceutically acceptable salt of the resultant compound of formula (I).

Examples of leaving groups $Q_1$, displaceable by a nucleophile, include halogen such as chloro and bromo, $C_{1-4}$ alkoxy, such as $CH_3O$ and $C_2H_5O-$, PhO—, or activated hydrocarbyloxy, such as $Cl_5C_6O-$ or $Cl_3CO-$.

If a group $Q_1$ is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group $Q_1$ is $C_{1-4}$ alkoxy, phenoxy or activated hydrocaroyloxy then the reaction is preferably carried out in an inert polar solvent, such as tolene or dimethylformamide. It is also preferred that the group $Q_1$ is $Cl_3CO-$ and that the reaction is carried out in toluene at reflux temperature.

When L is O the compound of formula (VI) may be in the form of a reactive derivative thereof, which is often a salt, such as the sodium or potassium salt.

The invention provides a further process for the preparation of a compound of formula (I) wherein X is N, or a pharmaceutically acceptable salt thereof, which process comprising cyclising a compound of formula (VIII):

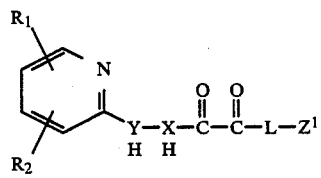

(VII)

wherein the variables are as hereinbefore defined; and thereafter optionally converting any $R_1$ and/or $R_2$ group to another $R_1/R_2$ group respectively, converting $Z^1$ when other than Z, to Z; and optionally forming a pharmaceutically acceptable salt of the resultant compound of formula (I).

The cyclisation reaction may be effected by heating in an inert solvent, such as xylene or decalin or heating with a dehydrating agent, such as phosphorus oxychloride.

A compound of formula (VII) may be prepared by the reaction of a compound of formula (VIII):

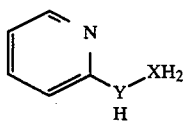

(VIII)

with a compound of formula (IX):

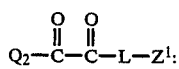

(IX)

wherein $Q_2$ is a leaving group and the remaining variables are as hereinbefore defined.

$Q_2$ is a leaving group as hereinbefore defined for $Q_1$ and the reaction is carried out in accordance with the conditions described herein for the reaction between the compounds of formulae (V) and (VI), wherein L is NH.

It will be apparent that compounds of the formula (I) containing an $R_1$ or $R_2$ group which is convertible to another $R_1$ or $R_2$ group are useful novel intermediates. i.e. a hydrogen substituent is convertible to a halogen substituent by halogenation using conventional halogenating agents.

$Z^1$ when other than Z may have a hydrogenolysable protecting group which is benzyl optionally substituted by one or two groups as defined for $R_1$ and $R_2$. Such benzyl groups may, for example, be removed, when $R_1$ or $R_2$ is not halogen, by conventional transition metal catalysed hydrogenolysis to give compounds of the formula (X):

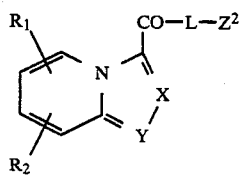

(X)

wherein $Z^2$ is of formula (d) or (e):

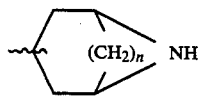

(d)

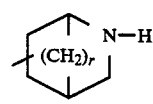

(e)

wherein the variables are as defined in formula (I).

This invention also provides a further process for the preparation of a compound of the formula (I) which comprises N-alkylating a compound of formula (X), and optionally forming a pharmaceutically acceptable salt, of the resulting compound of the formula (I).

In this further process of the invention 'N-alkylation' comprises the substitution of the N-atom depicted in formula (X) by any group $R_5/R_6$ as hereinbefore defined. This may be achieved by reaction of the compound of formula (X) with a compound $R_5Q_3$ or $R_6Q_3$ wherein $R_5$ and $R_6$ are as hereinbefore defined and $Q_3$ is a leaving group.

Suitable values for $Q_3$ include groups displaced by nucleophiles such as Cl, Br, I, $OSO_2CH_3$ or $OSO_2C_6H_4pCH_3$.

Favoured values for $Q_3$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slight above.

Alternatively, 'N-alkylation' may be effected under conventional reductive alkylation conditions when the group $R_5$ or $R_6$ in the compound of formula (I) contains a methylene group adjacent to the N-atom in the bicycle.

Interconverting $R_5$ or $R_6$ in the compound of the formula (X) before coupling with the compound of the formula (V) is also possible. Such interconversions are effected conveniently under tne above conditions. It is desirable to protect any amine function with a group readily removable by acidolysis such as a $C_{2-7}$ alkanoyl group, before $R_5/R_6$ interconversion.

When $R_5$ or $R_6$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_5$ or $R_6$ is methyl, where the methyl group is replaced by alkoxycarbonyl. Such compounds may then be reduced using a strong reductant such as lithium aluminium hydride to the corresponding compound of formula (V).

The compounds of formula (V), (VI), (VIII) and (IX) are known or are preparable analogously to, or routinely from, known compounds.

Compounds of the formula (VI) wherein Z is of formula (c) may be prepared as described in European Patent Publication No. 115933 or by analogous methods thereto. Compounds of the formulae (VII) and (X) are novel and form an aspect of the invention.

It will be realised that in the compound of the formula (I) the —CO—L— linkage may have an endo or exo orientation with respect to the ring of the bicyclic moiety to which it is attached. A mixture of endo and exo isomers of the compound of the formula (I) may be synthesised non-stereospecifically and the desired isomer separated conventionally therefrom e.g. by chromatography; or alternatively the endo and exo isomer may if desired by synthesised from the corresponding endo or exo form of the compound of the formula (VI).

Pharmaceutically acceptable salts of the compounds of this invention may be formed conventionally.

The salts may be formed for example by reaction of the base compound of formula (I) with a pharmaceutically acceptable organic or inorganic acid.

The compounds of the present invention are 5-HT antagonists and it is thus believed may generally be used in the treatment or prophylaxis of migraine, cluster headaches and trigeminal neuralgia; and also as anti-emetics, in particular that of preventing vomiting and nausea associated with cancer therapy, and motion sickness. Examples of such cancer therapy include that using cytotoxic agents, such as cisplatin, doxorubicin and cyclophosphamide, particularly cisplatin; and also radiation treatment. Compounds which are 5-HT antagonists may also be of potential use in the treatment of CNS disorders such as anxiety and psychosis; arrhythmia, obesity and gastrointestinal disorders such as irritable bowel syndrome.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diuents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include ediole oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of migraine, cluster headache, trigeminal neuralgia and/or emesis in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I); the following descriptions illustrate the preparation of intermediates.

DESCRIPTION 1

(endo)-N-(9-Methyl-9-azabicyclo[3,3,1]non-3-yl) ethyl oxamate (D1)

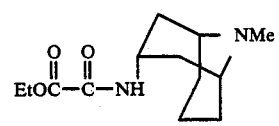

(D1)

To a stirred solution of (endo)-9-methyl-9-azabicyclo[3,3,1]-nonan-3-amine (5.0 g) and triethylamine (5 ml) in CH$_2$Cl$_2$ (200 ml) at 0° C. was added, dropwise, a solution of ethyl oxalyl chloride (4.0 ml) in CH$_2$Cl$_2$ (10 ml). After 1 h, the reaction mixture was washed with saturated NaHCO$_3$ solution (100 ml), dried (K$_2$CO$_3$) and concentrated in vacuo. Trituration of the residue with ether afforded the title compound (D.1) (5.3 g).

m.p. 105°–9° C.

$^1$H-nmr(CDCl$_3$)δ 7.0–6.5 (m, 1H), 4.2 (q superimposed on m, 3H), 3.2–2.8 (m, 2H), 2.6–0.8 (m, 16H including 2.40, s, 3H, and 1.35, t, 3H).

DESCRIPTION 2

(endo)-N-(9-Methyl-9-azabicyclo[3,3,1]non-3-yl)-N'-(2-pyridyl-methyl)oxamide (D.2)

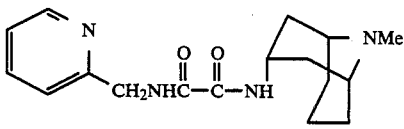

A solution of 2-aminomethyl pyridine (0.42 g) and (endo)-N-(9-methyl-9-azabicyclo[3,3,1]non-3-yl) ethyl oxamate (D.1) (1.0 g) in xylene (10 ml) were heated under reflux until the reaction was complete by T.L.C. The solvent was removed in vacuo and the residue triturated with ether/petrol to give the title compound (D.2) (0.63 g).

$^1$H-nmr(CDCl$_3$)δ 8.7–8.2 (m, 2H), 7.7–6.8 (m, 4H), 4.5 (d, 2H), 4.6–3.8 (m, 1H), 3.2–2.7 (m, 2H), 2.65–0.8 (m, 13H including 2.40, s, 3H).

EXAMPLE 1

(endo)-N-(9-Methyl-9-azabicyclo[3.3.1]non-3-yl) imidazo [1,5-a]-pyridine-3-carboxamide (E1)

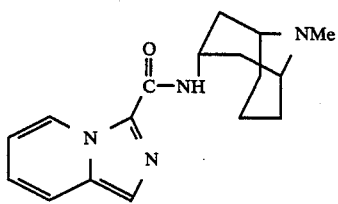

A solution of (endo)-N-(9-methyl-9-azabicyclo[3,3,1]non-3-yl)-N'-(2-pyridylmethyl)oxamide (D.2) (0.3 g) in xylene (10 ml) was treated with phosphoryl chloride (0.1 ml) and then heated under reflux for 18 h. The solvent was then removed by evaporation in vacuo and the residue partitioned between CH$_2$Cl$_2$ (100 ml) and K$_2$CO$_3$ solution. The organic extract was dried (K$_2$CO$_3$), evaporated and purified by column chromatography on silica to give the title compound (0.1 g).

$^1$H-nmr(d$^6$DMSO)δ: 9.45 (d, 1H), 8.00–7.75 (m, 1H), 7.63 (d, 1H), 7.46 (s, 1H), 7.00 (t, 1H), 6.85 (t, 1H), 4.60–4.40 (m, 1H), 3.20–3.00 (m, 2H), 2.54 (s, 3H), 2.45–2.27 (m, 2H), 2.15–1.90 (m, 3H), 1.65–1.40 (m, 3H), 1.05–1.00 (m, 2H).

m.s. M+ 298.1798; C$_{17}$H$_{22}$N$_4$O requires M+ 298.1793.

EXAMPLE 2

(endo)-N-(8-Methyl-8-azabicyclo[3.2.1]oct-3-yl) indolizin-3-carboxamide (E2)

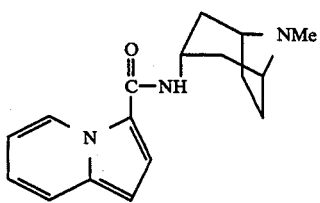

A solution of (endo)-8-methyl-8-azabicyclo[3,2,1]octan-3-amine) (1.0 g) and triethylamine (1.0 ml) in CH$_2$Cl$_2$ (10 ml) was added to a stirred solution of indolizin-1-carbonyl chloride (J. Chem. Soc. C. 901 [1969]) (1.4 g) in CH$_2$Cl$_2$ (100 ml). After 1 h, the reaction mixture was washed with K$_2$CO$_3$ solution, dried (K$_2$CO$_3$) and evaporated to dryness. Purification by column chromatography on alumina gave the title compound (0.5 g) mp 102°–3°

$^1$H-nmr(CDCl$_3$)δ: 9.56 (d, 1H); 7.45 (d, 1H), 7.06 (d, 1H), 6.92 (t, 1H), 6.72 (t, 1H), 6.45 (d, 1H), 6.25 (brd, 1H), 4.30 (q, 1H), 3.23 (brs, 2H), 2.50–2.10 (m, 7H including 2.34,s,3H), 2.00–1.70 (m, 4H).

m.s. M+ 283.1685; C$_{17}$H$_{21}$N$_3$O requires M+ 283.1685.

EXAMPLE 3

(endo)-N-(8-Methyl-8-azabicyclo[3.2.1]oct-3-yl)-1-methylindolizin-3-carboxamide (E3)

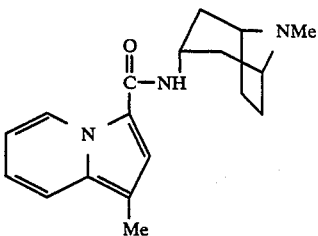

Following the precedures outlined in Example 2; 3-methyl-indolizin-1-carbonyl chloride (0.3 g) was converted to the title compound (E.3) (0.16 g) mp 169°–70°.

$^1$H-nmr(CDCl$_3$)δ; 9.52 (d, 1H) 7.38 (d, 1H), 6.88 (s, t, 2H), 6.67 (t, 1H), 6.17 (d, 1H), 4.28 (q, 1H), 3.25 (brs, 2H), 2.40–2.10 (m, 10H including 2.34,s,6H); 2.00–1.75 (m, 4H).

m.s M+ 297.1844; C$_{18}$H$_{23}$N$_3$O requires M+ 294.1841.

EXAMPLE 4

(endo)-N-(8-Methyl-8-azabicyclo[3.2.1]oct-3-yl)-2-methoxyindolizin-3-carboxamide (E4)

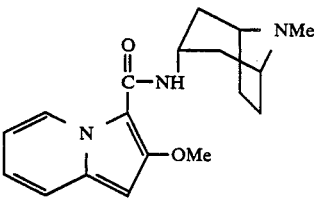

Following the procedures outlined in Example 2; 2-methoxy-indolizin-1-carbonyl chloride (0.3 g) was converted to the title compound (0.22 g)

$^1$H-nmr(CDCl$_3$)δ: 9.75 (d, 1H); 7.68 (d, 1H), 7.30 (d, 1H), 6.94 (t, 1H), 6.68 (t, 1H), 6.08 (s, 1H), 4.33 (q, 1H), 4.04 (s, 3H), 3.20 (brs, 2H), 2.40–2.22 (m, 5H including 2.34,s,3H), 2.20–2.05 (m, 2H), 2.00–1.85 (m, 2H).

m.s. M+ 313.1794; C$_{18}$H$_{23}$N$_3$O requires M+ 313.1790.

EXAMPLE 5

(endo)-N-(9-Methyl-9-azabicyclo[3.3.1]non-3-yl)-pyrido [2,1-c]-S-triazole-3-carboxamide (E5)

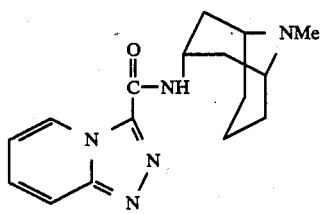
(E5)

A solution of (endo)-N-(9-methyl-9-azabicyclo[3.3.1]-non-3-yl)-N'-(2-pyridylamino)oxamide (prepared from 2-hydrazino-pyridine as in description 2) (2.0 g) was heated under reflux in a Dean and Stark apparatus in xylene (200 ml) with tosic acid (0.1 g) for 24 h. The xylene was removed and the residue partitioned between aqueous NaHCO$_3$ and CHCl$_3$ (200 ml). The chloroform extract was dried (K$_2$CO$_3$) and evaporated to dryness. Crystallisation of the residue from EtOAc/petrol afforded the title compound (E5) (1.2 g) m.p. 193°–4° C.

$^1$H-nmr (CDCl$_3$)δ: 9.36 (d, 1H), 7.86 (d, 1H), 7.41 (t, 1H), 7.33 (d, 1H), 7.02 (t, 1H), 4.65–4.45 (m, 1H), 3.14 (brd, 2H), 2.62–2.44 (m, 5H including 2.52, s, 3H); 2.10–1.90 (m, 3H), 1.60–1.35 (m, 3H), 1.05–1.00 (m, 2H).

Following the procedures outlined in Description 1, 2 and Example 1, the appropriately substituted pyridine and (endo)-8-methyl-8-azabicyclo[3.2.1]octan-3-amine were converted into the following compounds.

EXAMPLE 6

(endo)-N-(8-Methyl-8-azabicyclo[3.2.1]oct-3-yl)imidazo [1,5-a]pyridine-3-carboxamide monohydrochloride (E6)

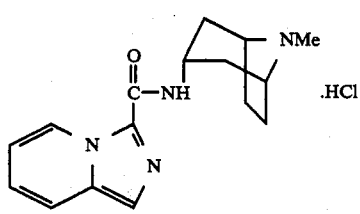
(E6)

$^1$H-nmr (d$^6$-DMSO)δ: 10.30 (br s, 1H), 9.35 (d, 1H), 8.43 (d, 1H), 7.82 (d, 1H), 7.63 (s, 1H), 7.20–7.00 (m, 2H), 4.10–4.00 (m, 1H), 3.90–3.70 (m, 2H), 2.64 (d, 3H), 2.40–2.10 (m, 7H).

m.s. M+ 284.1640; C$_{18}$H$_{20}$N$_4$O requires M+ 284.1649.

EXAMPLE 7

(endo)-N-(8-Methyl-8-azabicyclo[3.2.1]oct-3-yl)-1-methylimidazo[1,5-a]pyridine-3-carboxamide monohydrochloride (E7)

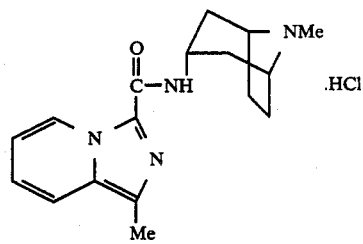
(E7)

$^1$H-nmr (CDCl$_3$) δ: 12.35 (br s, 1H), 9.46 (br d, 1H), 7.57 (d, 1H), 7.10–6.80 (m, 2H), 4.37 (q, 1H), 3.80 (br s, 2H); 3.25–3.10 (m, 2H), 2.77 (d, 3H), 2.70–2.10 (m, 10H).

m.s. M+ 298.1799: C$_{17}$H$_{22}$N$_4$O$_2$ requires M+ 298.1804.

Following the procedure outlined in Example 2: the following compounds were prepared.

EXAMPLE 8

(endo)-N-(8-Methyl-8-azabicyclo[3.2.1]oct-3-yl)-1-ethyl indolizin-3-carboxamide (E8)

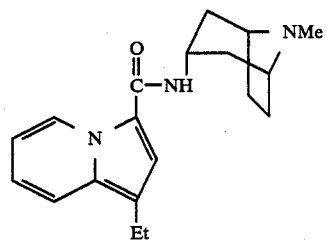
(E8)

m.p. 171°–2° C.

$^1$H-nmr (CDCl$_3$)δ: 9.53 (dm, 1H), 7.40 (dm, 1H), 6.92–6.82 (m, 2H including 6.89, s, 1H), 6.67 (tm, 1H), 6.19 (brd, 1H), 4.29 (q, 1H), 3.25 (brs, 2H), 2.76 (q, 2H), 2.40–2.15 (m, 7H including 2.33, s, 3H), 1.95–1.72 (m, 4H), 1.30 (t. 3H).

m.s. M+ 311.2007; C$_{19}$H$_{25}$N$_3$O requires 311.2017.

EXAMPLE 9

N-(3-Quinuclidinyl)-1-ethylindolizin-3-carboxamide (E9)

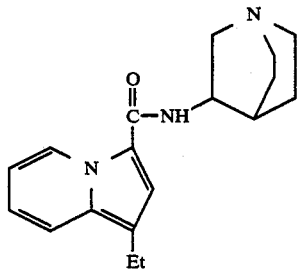
(E9)

m.p. 185°–6° C.

$^1$H-nmr (CDCl$_3$) δ: 9.54 (dm, 1H), 7.40 (dm, 1H), 7.05 (s, 1H), 6.89 (tm, 1H), 6.67 (tm, 1H), 6.03 (brd, 1H), 4.26–4.12 (m, 1H), 3.48 (d,d,d, 1H), 3.10–2.65 (m, 7H including 2.78, q, 2H), 2.12–2.05 (m, 1H), 1.92–1.70 (m, 3H), 1.64–1.50 (m, 1H), 1.30 (t, 3H).

m.s. M+ 297.1852; C$_{18}$H$_{23}$N$_3$O requires 297.1863.

EXAMPLE 10

(endo)-N-(8-Methyl-8-azabicyclo[3.2.1]oct-3-yl)-1-phenylindolizin-3-carboxamide (E10)

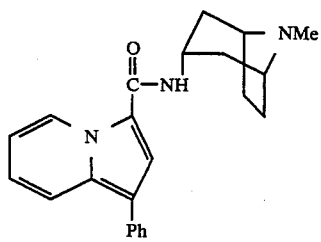

m.p. 148° C.

$^1$H-nmr (CDCl$_3$) δ: 9.65 (dm, 1H), 7.90–6.60 (m, 9H including 7.18, s, 1H), 6.30 (brd, 1H), 4.32 (q, 1H), 3.20 (brs, 2H), 2.55–1.60 (m, 11H including 2.34, s, 3H).

EXAMPLE 11

(endo)-N-(8-Methyl-8-azabicyclo[3.2.1]oct-3-yl)-1-methoxycarbonylindolizin-3-carboxamide (E11)

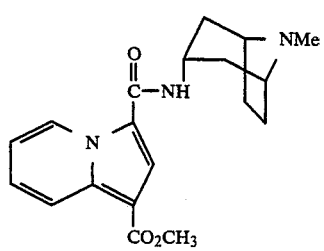

m.p. 183°–4° C., $^1$H-nmr (CDCl$_3$) δ: 9.68 (dm, 1H), 8.27 (dm, 1H), 7.55 (s, 1H), 7.28 (m, 1H), 6.90 (dt, 1H), 6.31 (brd, 1H), 4.28 (q, 1H), 3.94 (s, 3H), 3.22 (brs, 2H), 2.55–1.55 (m, 11H including 2.34, s, 3H).

EXAMPLE 12

(endo)-N-(8-Methyl-8-azabicyclo[3.2.1]oct-3-yl)-1-cyanoindolizin-3-carboxamide (E12)

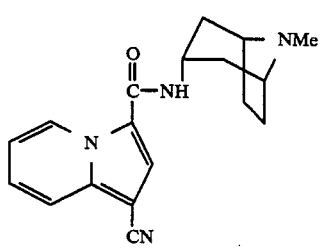

m.p. 194°–5° C.

$^1$H-nmr (CDCl$_3$) δ: 9.62 (dm, 1H), 7.70 (dm, 1H), 7.33 (s, 1H), 7.33–7.24 (m, 1H), 6.95 (dt, 1H), 6.33 (brd, 1H), 4.28 (q, 1H), 3.26 (brs, 2H), 2.41–2.20 (m, 7H including 2.33, s, 3H), 1.92–1.74 (m, 4H).

m.s M+ 308.1637; C$_{18}$H$_{20}$N$_4$O requires 308.1637.

EXAMPLE 13

(endo)-N-(8-Methyl-8-azabicyclo[3.2.1]oct-3-yl)-1-acetylindolizin-3-carboxamide (E13)

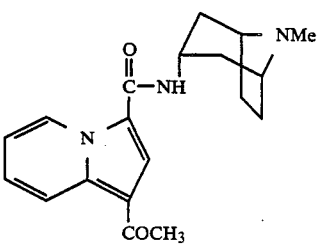

m.p. 162°–3° C.

$^1$H-nmr (CDCl$_3$) δ: 9.65 (d, 1H), 8.51 (d, 1H), 7.40 (s, 1H), 7.38–7.26 (m, 1H), 6.96 (t, 1H), 6.31 (brd, 1H), 4.31 (q, 1H), 3.25 (brs, 2H), 2.57 (s, 3H), 2.42–2.20 (m, 7H including 2.34, s, 3H), 1.95–1.75 (m, 4H).

m.s. M+ 325.1789; C$_{19}$H$_{23}$N$_3$O$_2$ requires 325.1788.

EXAMPLE 14

(endo)-N-(8-Methyl-8-azabicyclo[3.2.1]oct-3-yl)-1-nitroindolizin-3-carboxamide (E14)

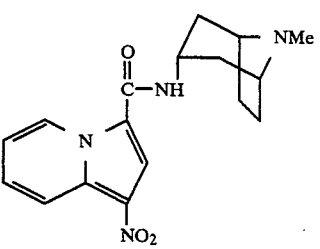

m.p. 183°–5° C., $^1$H-nmr (CDCl$_3$) δ: 9.74 (d, 1H), 8.49 (d, 1H), 7.80 (s, 1H), 7.54 (t, 1H), 7.09 (t, 1H), 6.52 (brd, 1H), 4.30 (q, 1H), 3.28 (brs, 2H), 2.50–2.15 (m, 7H including 2.35, s, 3H), 2.00–1.80 (m, 4H).

m.s. M+ 328.1534; C$_{17}$H$_{20}$N$_4$O$_3$ requires 328.1537.

Pharmacology

Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5-HT-evoked response to 50% of the control response (ED$_{50}$) was then determined.

The compounds of Examples 1 and 2 had an ED$_{50}$ value of 10 mg/μg i.v. and the compound of Example 3 had an ED$_{50}$ value of 1.6 μg/kg/ i.v.

I claim:
1. A compound of formula (I), or a pharmaceutically acceptable salt thereof:

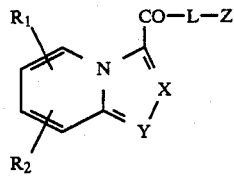

wherein
L is NH or O;
X is N or $CR_3$ wherein $R_3$ is hydrogen or $C_{1-6}$ alkoxy;
Y is N or $CR_4$ wherein $R_4$ is hydrogen, halogen, $CF_3$, $C_{1-6}$ alkyl, $C_{1-6}$ alkoxy, $C_{1-6}$ alkylthio, $C_{1-6}$ alkylsulphonyl, $C_{1-6}$ alkylsulphinyl, $C_{1-7}$ acyl, cyano, $C_{1-6}$ alkoxycarbonyl, $C_{1-7}$ acylamino, hydroxy, nitro or amino, aminocarbonyl, or aminosulphonyl, optionally N-substituted by one or two groups selected from $C_{1-6}$ alkyl, $C_{3-8}$ cycloalkyl, and $C_{3-8}$ cycloalkyl $C_{1-4}$ alkyl or disubstituted by $C_4$ or $C_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;
$R_1$ and $R_2$ are independently selected from hydrogen, or halogen;
Z is a group of formula (a), (b) or (c):

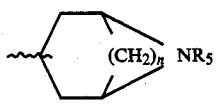

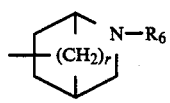

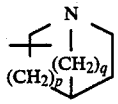

wherein
n is 2 or 3; p is 1 or 2; q is 1 to 3; r is 1 to 3; and $R_5$ or $R_6$ is $C_{1-4}$ alkyl.

2. A compound according to claim 1 of formula (II):

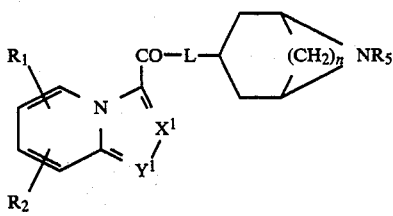

wherein $X^1$ is N, CH or $COCH_3$, $Y^1$ is N, or $C-R_4^1$ wherein $R_4^1$ is hydrogen, fluoro, chloro, bromo, $CF_3$, methyl, ethyl, methoxy, ethoxy, methylthio, ethylthio, methylsulphonyl, ethylsulphonyl, methylsulphinyl, ethylsulphinyl, acetyl, propionyl, cyano, methoxycarbonyl, ethoxycarbonyl, acetylamino, hydroxy, nitro; and amino, aminocarbonyl, or aminosulphonyl, any of which may be optionally substituted by one or two methyl groups or by a cyclopentyl or cyclohexyl group or $R_4^1$ is phenyl or benzyl optionally substituted by one or two methyl, methoxy, bromo, chloro or fluoro groups; and the remaining variables are as defined in claim 1.

3. A compound according to claim 2 wherein $R_5$ is methyl.

4. A compound according to claim 2 wherein $Y'$ is N, CH or $CCH_3$.

5. A compound according to claim 1 of formula (III):

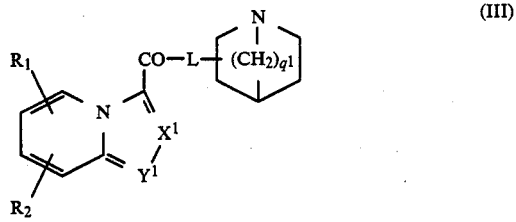

wherein $X^1$ is N, CH or $COCH_3$, $Y^1$ is N or $C-R_4^1$ wherein $R_4^1$ is hydrogen, fluoro, chloro, bromo, $CF_3$, methyl, ethyl, methoxy, ethoxy, methylthio, ethylthio methylsulphonyl, ethylsulphonyl, methylsulphinyl, ethylsulphinyl, acetyl, propionyl, cyano, methoxycarbonyl, ethoxycarbonyl acetylamino, hydroxy, nitro; and amino, aminocarbonyl, or aminosulphonyl, any of which may be optionally substituted by one or two methyl groups or by a cyclopentyl or cyclohexyl group or $R_4^1$ is phenyl or benzyl optionally substituted by one or two methyl, methoxy, bromo, chloro or fluoro groups; $q^1$ is 1 or 2; and the remaining variables are as defined in claim 1.

6. A compound according to claim 1 wherein $R_1$ and $R_2$ are both hydrogen.

7. A compound selected from the group consisting of:
(endo)-N-(9-methyl-9-azabicyclo[3.3.1]non-3yl-)imidazo[1,5-a]-pyridine-3-carboxamide,
(endo)-N-(8-methyl-8-azabicyclo[3.2.1]oct-3-yl)indolizin-3-carboxamide,
(endo)-N-(8-methyl-8-azabicyclo[3.2.1]oct-3-yl)-1-methylindolizin-3-carboxamide,
(endo)-N-(8-methyl-8-azabicyclo[3.2.1]oct-3-yl)-2-methoxyindolizin-3-carboxamide,
(endo)-N-(9-methyl-9-azabicyclo[3.3.1]non-3-yl)pyrido-[2,1-c]-S-triazole-3-carboxamide,
(endo)-N-(8-methyl-8-azabicyclo[3.2.1]oct-3-yl)imidazo[1,5-a]-pyridine-3-carboxamide,
(endo)-N-(8-methyl-8-azabicyclo[3.2.1]oct-3-yl)-1methylimidazo[1,5-a]pyridine-3-carboxamide,
(endo)-N-(8-methyl-8-azabicyclo[3.2.1]oct-3-yl)-1-ethylindolizin-3-carboxamide,
N-(3-quinuclidinyl)-1-ethylindolizin-3-carboxamide,
(endo)-N-(8-methyl-8-azabicyclo[3.2.1]oct-3-yl)-1-phenylindolizin-3-carboxamide,
(endo)-N-(8-methyl-8-azabicyclo[3.2.1]oct-3-yl)-1-methoxycarbonylindolizin-3-carboxamide,
(endo)-N-(8-methyl-b 8-azabicyclo[3.2.1]oct-3-yl)-1-cyanoindolizin-3-carboxamide,
(endo)-N-(8-methyl-8-azabicyclo[3.2.1]oct-3-yl)-1-acetylindolizin-3-carboxamide,
(endo)-N-(8-methyl-8-azabicyclo[3.2.1]oct-3-yl)-1-nitroindolizin-3-carboxamide,
and pharmaceutically acceptable salts of any of the foregoing.

8. A pharmaceutical composition for use in the treatment of migraine, cluster headache, trigeminal neuralgia or emsis in mammals, comprising an effective amount of a compound according to claim 1, and a pharmaceutically acceptable carrier.

9. A method of treatment of migraine, cluster headache, trigeminal neuralgia or emesis, in mammals, which method comprises the administration of an effective amount of a compound according to claim 1.